US008277411B2

(12) United States Patent
Gellman

(10) Patent No.: US 8,277,411 B2
(45) Date of Patent: Oct. 2, 2012

(54) NEEDLE DEVICE

(75) Inventor: Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2904 days.

(21) Appl. No.: 10/062,357

(22) Filed: Jan. 31, 2002

(65) Prior Publication Data
US 2003/0144594 A1   Jul. 31, 2003

(51) Int. Cl.
*A61M 37/00* (2006.01)
(52) U.S. Cl. .................... 604/131; 604/272
(58) Field of Classification Search ............ 604/131, 604/271; 600/466, 167; 606/185
See application file for complete search history.

(56) References Cited

U.S. PATENT DOCUMENTS

| 3,941,121 | A | * | 3/1976 | Olinger et al. ........... 600/167 |
| 3,961,621 | A | | 6/1976 | Norheved .................. 128/2 B |
| 4,222,375 | A | | 9/1980 | Martinez ..................... 128/23 |
| 4,340,365 | A | | 7/1982 | Pisanu ........................ 433/80 |
| 4,566,438 | A | | 1/1986 | Liese et al. ................... 128/6 |
| 4,624,243 | A | * | 11/1986 | Lowery et al. ............ 600/136 |
| 4,675,004 | A | | 6/1987 | Hadford et al. .............. 604/44 |
| 4,808,157 | A | | 2/1989 | Coombs ....................... 604/44 |
| 4,935,008 | A | | 6/1990 | Lewis, Jr. ..................... 604/52 |
| 4,945,895 | A | | 8/1990 | Takai et al. .................... 128/6 |
| 4,959,063 | A | | 9/1990 | Kojima ...................... 606/15 |
| 5,127,916 | A | * | 7/1992 | Spencer et al. ............ 606/185 |
| 5,160,319 | A | | 11/1992 | Emery et al. ................ 604/27 |
| 5,199,431 | A | | 4/1993 | Kittrell et al. ............. 128/634 |
| 5,236,423 | A | * | 8/1993 | Mix et al. .................. 604/271 |
| 5,271,380 | A | | 12/1993 | Riek et al. ..................... 128/4 |
| 5,280,788 | A | | 1/1994 | Janes et al. ................ 128/665 |
| 5,370,640 | A | * | 12/1994 | Kolff ............................ 606/2 |
| 5,385,572 | A | | 1/1995 | Nobles et al. ............. 606/185 |
| 5,582,190 | A | | 12/1996 | Slavin et al. .............. 128/898 |
| 5,632,740 | A | | 5/1997 | Koch et al. ................... 606/4 |
| 5,645,537 | A | | 7/1997 | Powles et al. .............. 604/240 |
| 5,733,316 | A | | 3/1998 | Tierney et al. ............. 607/101 |
| 5,735,813 | A | | 4/1998 | Lewis ........................ 604/43 |
| 5,848,998 | A | | 12/1998 | Marasco, Jr. ............... 604/290 |
| 5,858,009 | A | | 1/1999 | Jonkman .................... 604/264 |
| 5,860,942 | A | | 1/1999 | Cox ........................... 601/155 |
| 6,036,116 | A | * | 3/2000 | Bui ............................ 239/432 |
| 6,039,693 | A | * | 3/2000 | Seward et al. ............. 600/459 |
| 6,053,899 | A | * | 4/2000 | Slanda et al. .............. 604/500 |
| 6,064,914 | A | | 5/2000 | Trachtenberg ............. 607/102 |
| 6,106,521 | A | | 8/2000 | Blewett et al. .............. 606/41 |
| 6,203,557 | B1 | | 3/2001 | Chin ........................... 606/190 |
| 6,224,378 | B1 | | 5/2001 | Valdes et al. ............... 433/224 |
| 6,258,061 | B1 | * | 7/2001 | Drasler et al. ............. 604/131 |
| 6,264,670 | B1 | | 7/2001 | Chin ........................... 606/190 |

* cited by examiner

*Primary Examiner* — Kevin C Sirmons
*Assistant Examiner* — Phillip Gray
(74) *Attorney, Agent, or Firm* — Brown Rudnick LLP

(57) ABSTRACT

A needle device for penetrating body tissues while substantially reducing the risk of damage to blood vessels and body organs by using visual control of the operative tip during insertion and the procedure, is disclosed herein. The needle device of the present invention has a large and diverse applicability to a number of medical procedures by enabling internal visual inspection of body tissues and cavities during treatment without open surgery or supplemental penetrating or visualization devices.

23 Claims, 10 Drawing Sheets

NEEDLE DEVICE

TECHNICAL FIELD

The present invention generally relates to devices for percutaneous diagnostic and therapeutic procedures, and, more particularly, to a multi-lumen needle device incorporating an optical element for continuously visualizing placement of the operative tip of the device during the procedure.

BACKGROUND INFORMATION

Percutaneous needle devices are used in a number of medical procedures, where access to body cavities or organs is desired. Such needle devices typically have a hollow shaft ending in a point, which serves to pierce the body tissue. After inserting the device to the target body cavity or organ, the hollow shaft may be used as a channel to take a fluid sample from the target site, aspirate, irrigate or deliver medicaments and other materials to the target site.

Despite the use of preliminary exploratory measuring procedures such as ultrasound and X-ray, it is extremely difficult for a medical professional to determine the positional relationship of the tip of the needle to an internal organ or body cavity to be treated. Moreover, blind percutaneous insertion of the needle device entails the risk of damaging blood vessels, puncturing organs, or tearing tissue as the needle is directed toward the target.

Typically, when percutaneous insertion of the treating instrument is desired, a puncture needle and a stylet are inserted in the target area without visualization of the piercing tip. Subsequently, the stylet is withdrawn and a multi-lumen endoscope or catherer are inserted. This may prolong and complicate the procedure, as well as cause inconvenience to a patient. Furthermore, as described above, initial unguided insertion of a puncture needle increases a risk of damaging blood vessels and internal organs.

While it is desirable that surgical instruments have a minimum diameter, the small diameter of instruments heretofore resulted in functional limitations. To overcome this deficiency, additional viewing instruments are often inserted to the target site. Such additional instruments, however, are typically too large to be successfully used in many medical procedures involving percutaneous devices.

It is, thus, desirable to provide a penetrating needle device that allows visualization of the target tissue simultaneous with application of diagnostic and treatment procedures. Thus, there is a need in the art for a low profile needle device capable of penetrating body tissues and enabling a medical professional to perform a number of diagnostic and therapeutic procedures percutaneously with a precise degree of control without resort to essentially blind approaches to the target tissue.

SUMMARY OF THE INVENTION

It is an object of the present invention to provide a versatile diagnostic and treatment needle device useful for inspection and treatment of internal body tissues, including removing material within a body such as calculi, hydrodissection of tissue planes, tissue cutting, flushing and debridement, and percutaneous injection of bulking materials, while substantially reducing the risk of damage to blood vessels and body organs.

Further, it is an object of the present invention to provide a versatile diagnostic and treatment needle device capable of percutaneous approaches to body cavities while providing continuous visual supervision of the surgical field, control of the insertion of the device, and performance of a therapeutic procedure through an operative channel of the device.

Finally, it is an object of the present invention to provide a versatile diagnostic and treatment needle device which is miniature enough to be acceptable for introduction into and visualization of tissue areas, which are difficult to otherwise access without resorting to open surgery techniques or to essentially blind guidance techniques.

Accordingly, a low profile needle device for penetrating body tissues while substantially reducing the risk of damage to blood vessels, nerves, and body organs by enabling the visualization and control of the operative tip during insertion and the procedure, is disclosed herein. The needle device of the present invention has a large and diverse applicability to a number of medical procedures because it enables internal visual inspection of body tissues and cavities at the treatment site without resorting to open surgery or to the simultaneous introduction or supplemental penetrating of visualization devices at the treatment site.

The needle device is adapted for applying hydrodynamic spray to the inside surface of the kidney or other tissue such as peri-prostatic tissue to irrigate the surface or debride tissue therefrom, or in between body organs or tissue to dissect the tissue planes. The needle device of the present invention is also useful for efficient percutaneous injections of bulking material into the urinary bladder wall, urethral wall or tissues surrounding the bladder or urethra.

The present invention enables the physician to observe the advance of the operative pointed tip of the device, thereby assisting the physician in controlling the path of the needle device and rate of its advance, as well as permits the physician to observe the tissues in front of the tip in order to avoid damage to vessels, nerves, and organs. In addition, the invention permits the physician to visualize the opening of the operative channel during the procedure. Because of its convenient size and low profile, the device of the present invention performs the above-described functions without compromising maneuverability and ease of use.

In general, in one aspect, the invention features a needle device, consisting of a supply tube and a nozzle with a tissue piercing point at its distal end. The tissue-piercing point of the nozzle may be adapted to penetrate skin, rectus, bladder wall and bladder neck of a patient. In one embodiment, the tissue piercing point may be reinforced.

A first lumen, axially formed in the nozzle, is connected to the distal end of the supply tube and has a first opening at the distal end of the nozzle. A second lumen axially formed in the nozzle has a second opening near the distal end of the nozzle. The second opening is positioned proximal to the tissue piercing point of the nozzle and proximal to the first opening. At least one optical element is axially positioned in the second lumen for transmitting and receiving optical radiation through the second opening in the nozzle.

Embodiments of this aspect of the invention include the following features. In one embodiment, the nozzle is a hollow tubular member having a first tube and a second tube axially disposed therein defining the first lumen and the second lumen respectively. In another embodiment, the nozzle consists of a base cylindrical member and a auxiliary cylindrical member, axially extending from the base cylindrical member at the distal end of the nozzle. The first lumen is axially formed in and extends through the base cylindrical member and the auxiliary cylindrical member. The second lumen is axially formed in and extends through the base cylindrical member.

In one embodiment, the needle device may also include a suction apparatus. The needle device may contain a handle at the proximal end of the nozzle. In one embodiment, the needle device may include a pressurizer for transporting fluids under pressure through the tube, the nozzle and through the first opening. The pressurizer may be pneumatic or hydraulic, for example, a bladder pump, a piston pump, and an impeller pump. In another embodiment, the pressurizer intermittently pressurizes the fluid delivered through the first opening. In yet another embodiment, the pressurizer delivers pressurized fluid through the first opening at a rate sufficient to dissect tissue planes.

In one embodiment, the second opening is substantially perpendicular to the longitudinal axis of the nozzle and proximal to the distal end of the nozzle. In a particular embodiment, the auxiliary cylindrical member curves inward at its distal end so that the first opening of the first lumen of the nozzle is substantially parallel to the longitudinal axis of the nozzle and the tissue piercing point is adjacent and distal to said first opening.

In one embodiment, the optical element positioned in the second lumen of the nozzle may be an image transmitting bundle of fiber-optic rods. The optical element may also include a fish-eye lens positioned at the second opening. Further, the needle device may include a plurality of illumination transmitting fiber-optics rods. In one embodiment, the illumination transmitting fiber-optics rods may be disposed in the second lumen. In another embodiment, the illumination transmitting fiber-optics rods may be positioned in the space between the hollow tubular member of the nozzle and the first and the second tubes.

In one embodiment, the device further consists of a syringe for holding bulking material. Non-limiting examples of such bulking material include collagen, silicone particles, ceramic balls, and fluoropolymer particles. In use, the pressurizer transports the bulking implant material under pressure from the reservoir through the nozzle and the first opening.

BRIEF DESCRIPTION OF THE DRAWINGS

In the drawings like reference characters generally refer to the same parts throughout the different views. The drawings are not necessarily to scale, emphasis instead generally being placed upon illustrating the principles of the invention.

DETAILED DESCRIPTION

A feature common to each of the embodiments of the needle device according to the invention described below is a multi-lumen nozzle with a tissue-piercing point. At least one lumen in the nozzle is a working channel, for example, for aspiration, flushing or introduction of a surgical instrument. At least one other lumen has an optical system. The optical system is positioned in the nozzle to enable an operator to view the tissue piercing point during a surgical procedure.

Figure 1:
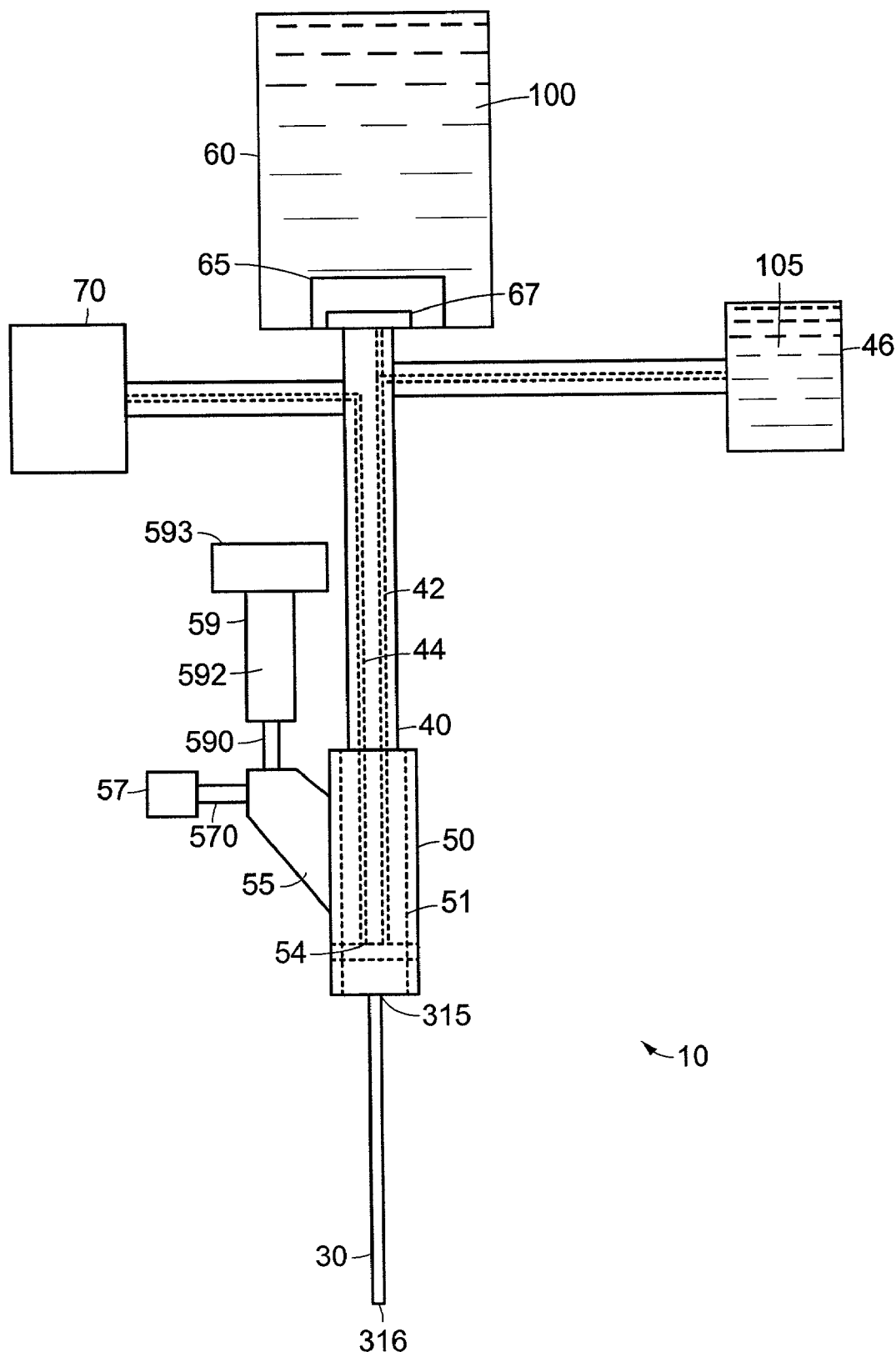
FIG. 1 illustrates a schematic view of the needle device according to one embodiment of the present invention.

Referring to FIG. 1, a needle device 10 includes a multi-lumen nozzle 30 connected to a reservoir 60 by a supply tube 40. The reservoir 60 supplies fluid 100 under pressure through the supply tube 40 to the nozzle 30, which directs the pressurized fluid 100 onto a target body site in the patient. In one embodiment of the present invention, the needle device 10 also includes a suction apparatus 70 connected to the nozzle 30, for example, through the supply tube 40 to enable aspiration through the nozzle 30. In this embodiment of the invention the supply tube 40 may have two lumens 42 and 44 where one lumen 42 is used for flushing, and the other lumen 44 for aspiration of the target body site.

In one embodiment, according to the invention, the reservoir 60 contains fluid 100, for example, water, Ringer's solution, or a balanced salt solution such as saline solution. The fluid 100 may contain medications 105, for example, antibiotics. In one embodiment, medications 105 are added to the reservoir 60. In another embodiment, the needle device 10 includes a container 46 with medications 105 connected to the nozzle 30 through the supply tube 40. In this embodiment, medications 105 are supplied to the flow of the fluid 100 in the lumen 42 of the supply tube 40 from the container 46. In another embodiment, the fluid 100 contains bulking material such as collagen, silicone particles, ceramic balls, or fluoropolymer particles, for example, polytetrafluoroethylene particles sold under the trademark TEFLON® by E.I. du Pont de Nemours and Company of Wilmington, Del.

Referring still to FIG. 1, in another embodiment of the needle device 10 according to the invention, a pressurizer 65 is submerged in the reservoir 60. The pressurizer 65 transfers fluid 100 from the reservoir 60 under pressure and delivers fluid 100 to the nozzle 30 through the lumen 42 in the supply tube 40. In one embodiment of the invention, the pressurizer 65 is an electric multi-stage rotary hydraulic pump, for example, a bladder pump, piston pump, or impeller pump. Other hydraulic pumps known in the art can also be used. In another embodiment, the pressurizer 65 is a pneumatic pump. In yet another embodiment, the reservoir 60 is pressurized by a pressurizer external to the reservoir 60. In yet another embodiment of the invention, the reservoir 60 is an intravenous fluid bag. Pressure may be applied to the intravenous fluid bag manually, by gravity, a pressure cuff, or by means of a pressurized chamber. In still another embodiment, a gas, for example, oxygen, carbon dioxide, or nitrogen, may be used in place of fluid 100.

With continued reference to FIG. 1, in one embodiment of the invention, the pressurizer 65 may include a pulsatile flow generator 67 to intermittently change the pressure of the flow of fluid 100 delivered to the nozzle 30. Suitable pulsatile flow generators may include, but are not limited to, for example, an ultrasonic vibrator, valving system, gas-assist system, and piezoelectric actuator. In one embodiment, the pulsatile flow generator 67 is flutter valve, activated by the fluid flow that rhythmically opens and closes to intermittently change the pressure of the flow of fluid 100.

Referring still to FIG. 1, in one embodiment, a handle 50 having a lumen 51 therein is attached to the supply tube 40 to enable manipulation of the nozzle 30 inside the patient's body. A proximal end 315 of the nozzle 30 is in fluid communication with at least one lumen 42 of the supply tube 40. The handle 50 may also contain or be connected to a control system (not shown) to control the pressurizer 65, pulsatile flow generator 67 and suction apparatus 70 to manage the pressure and direction of fluid 100, as well as pulsation and aeration of the flow. The control system of the handle 50 may also permit switching between flushing and aspiration modes.

As illustrated in FIG. 1, the handle 50 includes a port 55 for introducing optical elements. Attached to the port 55 are a light source 57 and an ocular system 59. Suitable light sources may include, but are not limited to, for example, a high-intensity tungsten filament lamp with fan cooling, or a halogen lamp. The light source 57 is in optical communication with a distal end 316 of the nozzle 30 through illumination fiber-optics rods, to be described below, axially positioned in a connecting tube 570, the lumen 51 in the handle 50, and the nozzle 30. The light source 57 provides illumination to the target site inside the patient's body. The ocular system 59, which includes an objective 592 and a focusing system 593, is in optical communication with the distal end 316 of the nozzle 30 through the image-transmitting fiber-optics bundle, to be described below, in a connecting tube 590, the lumen 51 in the handle 50, and the nozzle 30. The ocular system 59 permits an operator to visualize the distal end 316 of the nozzle 30 when the nozzle 30 is positioned inside the patient's body during a surgical procedure as will later be described.

Figure 2:
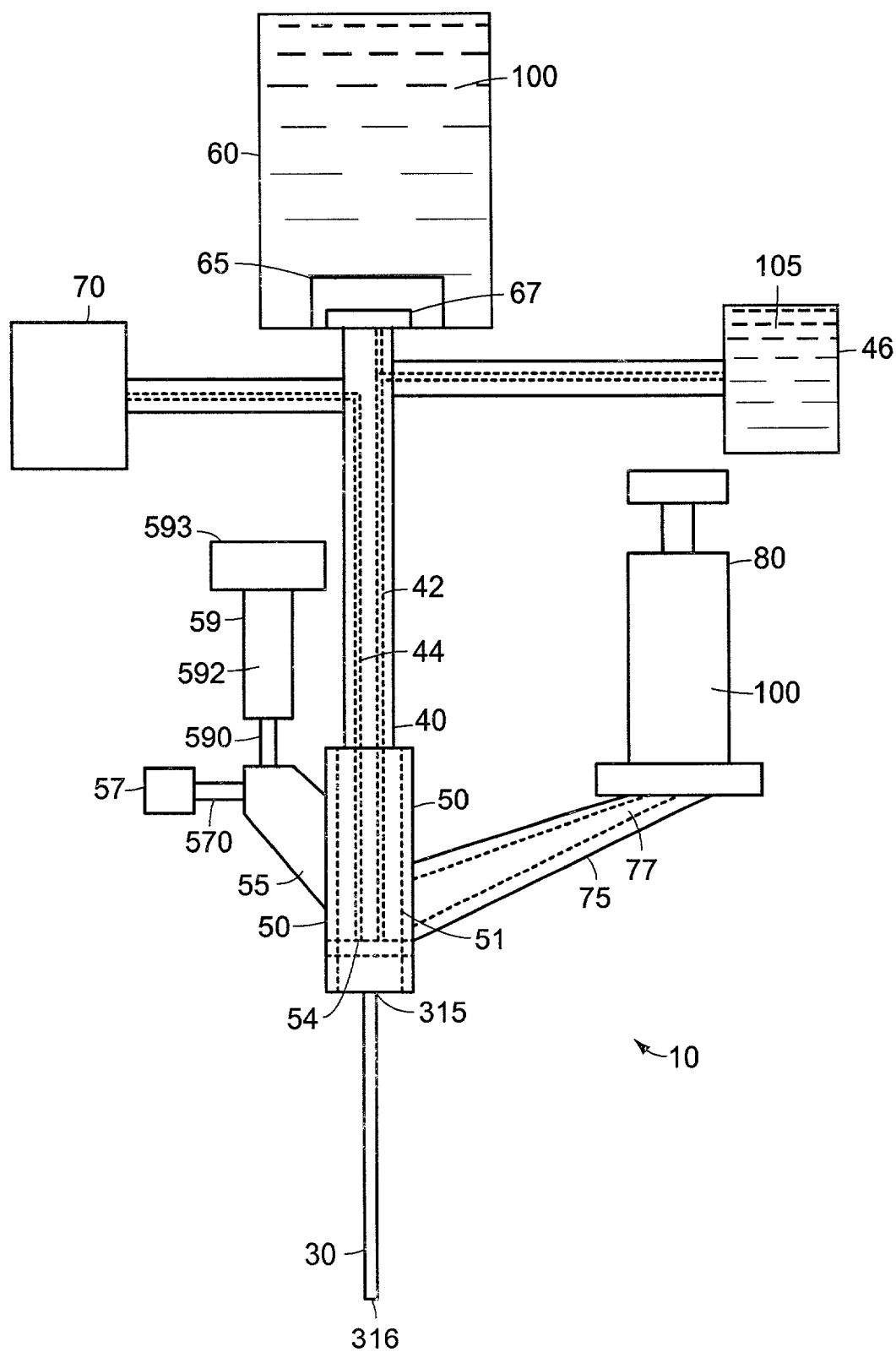
FIG. 2 illustrates a schematic view of the needle device according to another embodiment of the present invention.

Referring to FIG. 2, in another embodiment of the invention, a needle device 10, according to the invention, includes a syringe 80 containing fluid 100. In one embodiment, the syringe 80 is affixed to the handle 50 through a port 75 having a lumen 77, such as a Luer port. The barrel of the syringe 80 is in fluid communication with the lumen 51 in the handle 50 and the nozzle 30. In one embodiment of the invention, the fluid 100 is preferably a bulking material to be injected, for example, into the submucosal tissues of the urethra and/or the bladder neck and into tissues adjacent to the urethra for treatment of, for example, intrinsic sphincter deficiency. In this embodiment of the invention, a control system of the handle 50 includes a flow control subsystem, for example, a three-way valve (not shown), which allows the operator to switch between reservoir 60 and syringe 80 as sources of fluid 100.

Figure 3:
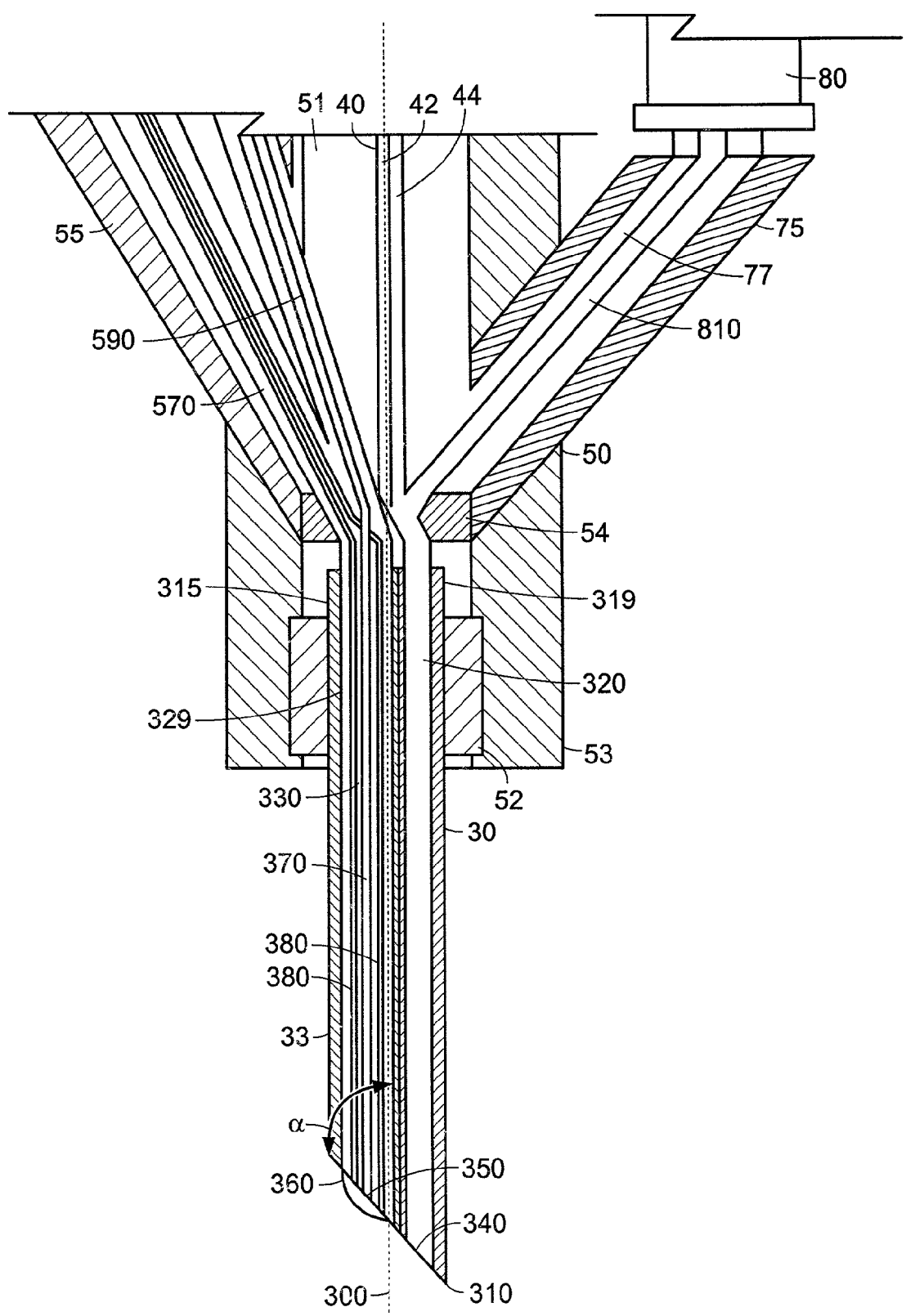
FIG. 3 illustrates a longitudinal cross-sectional view of the nozzle and its attachment to the handle according to the one embodiment of the present invention.

In another embodiment of the invention, referring to FIG. 3, the nozzle 30 has a proximal end 315, which is secured to the handle 50, for example, by means of a mounting member 52 disposed in the distal end 53 of the handle 50. In one embodiment, the nozzle 30 has a hollow tubular member 33. The tubular member 33 is formed from, for example, a stainless steel tube, having an outside diameter from 0.050 to 0.275 inches, preferably 0.100 inches, an inside diameter from 0.033 to 0.175 inches, preferably 0.085 inches, and a wall thickness from 0.0035 to 0.010 inches, preferably 0.006 inches. The nozzle 30 has a bevel 312 ranging from 0° to 45° angle α from the plane of the longitudinal axis 300 of the nozzle 30. The bevel 312 forms a tissue piercing point 310 at the distal end 316 of the nozzle 30. The tissue piercing point 310 is adapted to penetrate body tissues, including skin, rectus, bladder wall and bladder neck. In one embodiment of the invention, the tissue piercing point 310 is reinforced by, for example, a cobalt-chromium alloy to improve, for example, edge holding, durability and strength of the tissue piercing point 310.

Referring still to FIG. 3, in one embodiment according to the invention, disposed within the nozzle 30 are the second tube 329 defining an axially disposed second lumen 330, and an operative channel comprising a first tube 319 defining an axially disposed first lumen 320. In the preferred embodiment, the first tube 319 and the second tube 329 are substantially parallel and substantially adjacent to each other. The second tube 329 is made of any suitable material, for example, stainless steel or polyimide, and has an outside diameter from 0.020 to 0.100 inches, preferably 0.050 inches, an inside diameter from 0.015 to 0.090 inches, preferably 0.040 inches, and a wall thickness from 0.003 to 0.010 inches, preferably 0.005 inches. The first tube 319 is also made from any suitable material, for example, stainless steel or polymide, and has an outside diameter of from 0.050 to 0.150 inches, preferably 0.100 inches, an inside diameter from 0.040 to 0.140 inches, preferably 0.090 inches, and a wall thickness from 0.002 to 0.010 inches, preferably 0.005 inches. The first tube 319 and the second tube 329 extend proximal to the proximal end 315 of the nozzle to a connector 54 in the distal end of the handle 50 as will be described below. In another embodiment, the first lumen 320 and the second lumen 330 may be formed as an integral part of the nozzle, for example, by an extrusion process.

Figure 4:
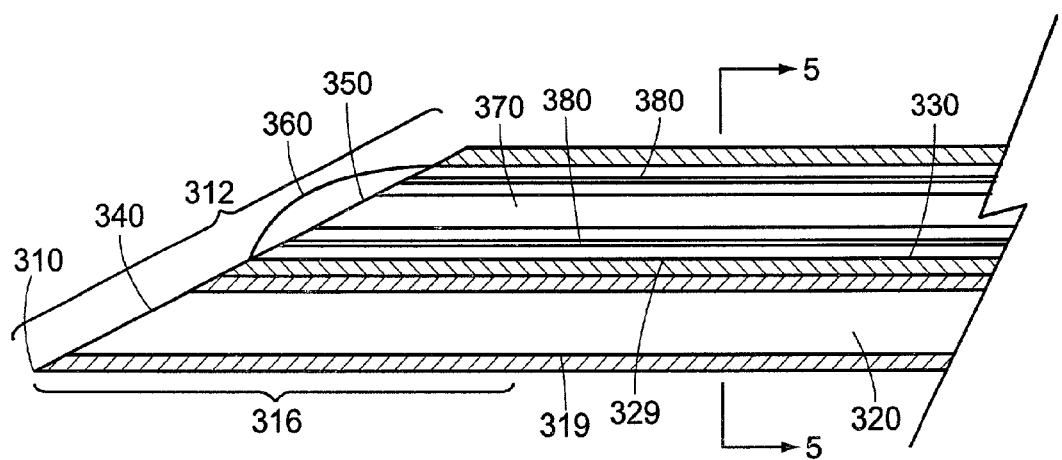
FIG. 4 illustrates an enlarged longitudinal cross-sectional view of the distal end of the nozzle according to the embodiment the present invention shown in FIG. 3.

Referring to FIG. 4, the first lumen 320 of the first tube 319 has a first opening 340 at the distal end 316 of the nozzle 30 substantially adjacent to the tissue piercing point 310. The second lumen 330 has a second opening 350 proximal to the tissue piercing point 310 and proximal to the first opening 340 so that the first opening 340 is positioned distal to the second opening 350 and the tissue piercing point 310. The openings 340 and 350 are disposed in the bevel 312 at the distal end 316 of the nozzle 30.

Referring still to FIG. 4, a lens system 360 is joined to the distal end of the tube 329 at the second opening 350. In a particular embodiment, the lens system 360 includes a wide-angle plano-convex lens, also known as a "fish-eye" lens, made from any suitable material, such as glass having, for example, a glass index of 1.62.

Referring still to FIG. 4, in one embodiment, an image transmitting bundle 370 of fiber-optic rods or fibers is disposed within the second lumen 330. In order to provide a high quality resolution for viewed objects, the smallest flexible fiber-optic fibers available in the making of the bundle 370 are used. Such bundles are usually produced by a drawing technique where a bundle of fibers is heated and the fibers are drawn at a specific drawing pressure and rate so that the bundle is elongated and the diameter of the fibers is reduced to achieve a predetermined diameter. In a particular embodiment, each of the individual fibers of the bundle 370 is approximately 6 microns in diameter. The preferred diameter of individual fiber rods in the bundle 370 is in the range from approximately 4 microns to about 10 microns. Additionally, the fibers in the bundle 370 can be made from any suitable material, including glass or plastic. The diameter of the fiber-optic bundle 370 is in the range from about 200 microns to 600 microns, preferably from about 300 microns to 500 microns. For descriptive purposes in this application, the term "rods" is used to define optic fibers of the type referred to herein, for example, flexible optic fibers.

Figure 5:
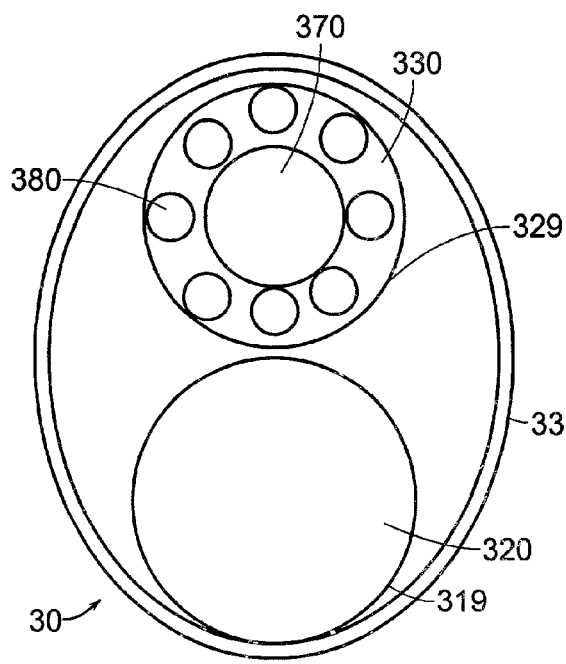
FIG. 5 illustrates a cross-sectional view along the line 5-5 of FIG. 4 according to one embodiment of the present invention.

Further, referring now to FIG. 5, a cross-section of an embodiment of the nozzle 30, illustrated in FIG. 4, is shown. A plurality of illumination transmitting fiber-optic rods or fibers 380 is axially disposed in the nozzle 30. There are typically about 6,000 fiber-optic rods in the fiber-optic bundle. In a particular embodiment, the rods 380 are positioned within the second lumen 330 and extend from the second opening 350 of the nozzle 30 to the light source 57 (shown in FIGS. 1-2). In one embodiment of the invention, the nominal diameter of the bundle 370 is 375 microns. In another embodiment, the rods 380 having diameters ranging from 0.003 to 0.008 inch are bundled in a plurality of bundles 370 having diameters ranging from 0.020 to 0.030 inches.

Figure 6:
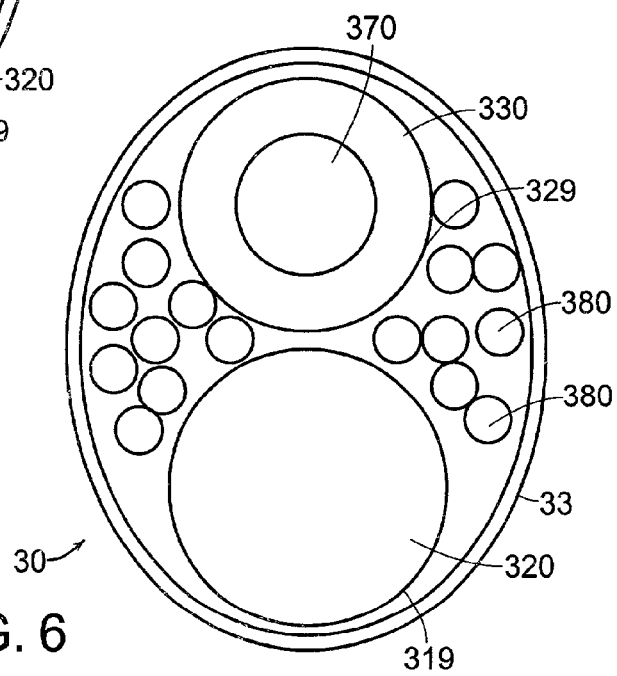
FIG. 6 illustrates a cross-sectional view along the line 5-5 of FIG. 4 according to another embodiment of the invention.

Referring now to FIG. 6, another embodiment of the illumination transmitting fiber-optic rods 380 is illustrated. A plurality of rods 380 is axially disposed within the nozzle 30 outside of and parallel to the lumens 320 and 330 of the tubes 319 and 329 respectively. The rods 380 extend from the distal end 316 of the nozzle 30 to the light source 57 (shown in FIGS. 1-2).

Referring again to FIG. 3, the fiber-optic bundle 370 and the plurality of rods 380 exit from the proximal end 315 of the nozzle 30 into the connector 54 and then into the port 55 through the connecting tubes 570 and 590. The proximal ends of the rods 380 pass through port 55 and are in optical communication with the light source 57 shown on FIGS. 1-2. Light is transmitted from the light source 57 through the distal end 316 of the nozzle 30 onto the target body site. The proximal end of the fiber optic bundle 370 is in optical communication with the ocular system 59 shown in FIGS. 1-2 to permit visualization of an image, such as a composite image, transmitted by the lens system 360 to the proximal end of the bundle 370. In order that the image transmitted by the lens system 360 is precisely focused on the proximal end of the bundle 370, the bundle 370 can be reciprocated axially within the lumen 330 to compensate for objects viewed at varying distances from the second opening 350 of the nozzle 30.

Referring to FIG. 4, in one embodiment of the invention, the first opening 340 is positioned distal to the second opening 350 between the second opening 350 and the tissue piercing point 310. Such configuration of the tissue piercing point 310, and the opening 350 enables an operator to observe the tissue piercing point 310 as it advances in the patient's body, as well as to observe the first opening 340.

Referring again to FIGS. 1-2, the fluid 100 may be held in the reservoir 60 or the syringe 80. Referring again to FIG. 3, in one embodiment, the lumen 320 of the nozzle 30 is in fluid communication with the reservoir 60 shown in FIG. 1 through the supply tube 40 and the connector 54 in the handle 50. In another embodiment, the lumen 320 of the nozzle 30 is in fluid communication with the syringe 80, through a connecting tube 810, axially disposed in the lumen 77 of the port 75, and the connector 54. In one embodiment, the connector 54 contains a flow control system (not shown), which allows an operator to connect the first lumen 320 alternatively to the supply tube 40 or to the syringe 80 as needed.

Figure 7:
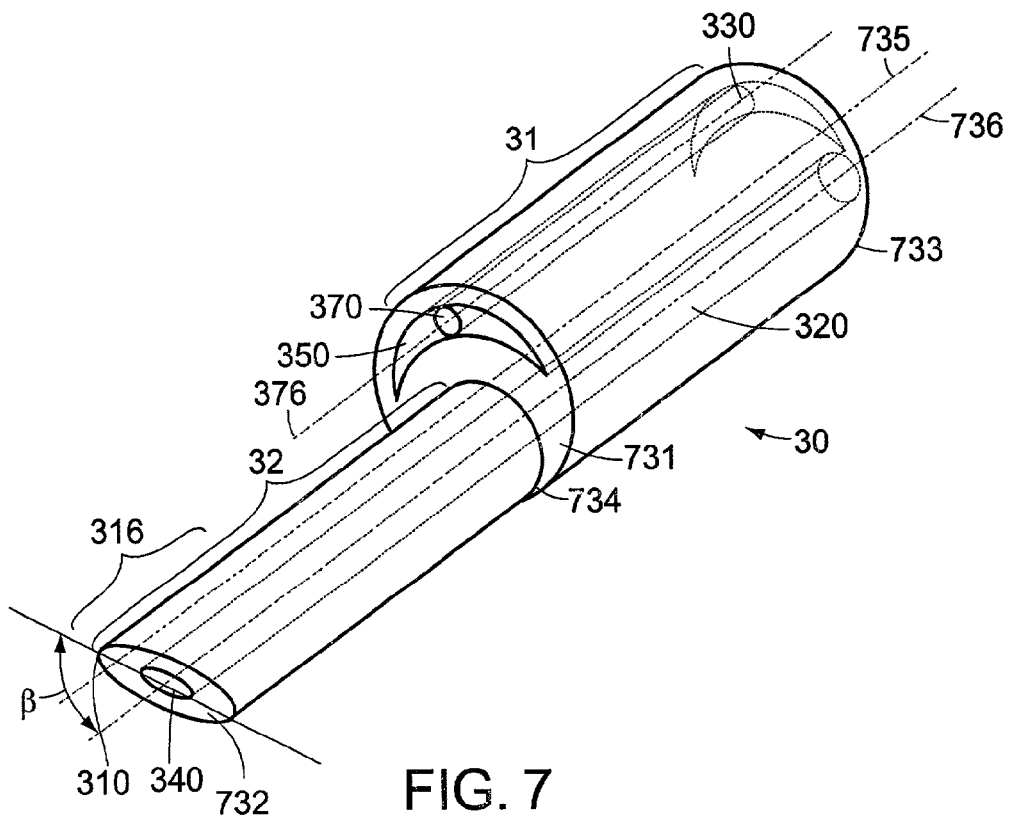
FIG. 7 illustrates a perspective view of the distal end of the nozzle according to another embodiment of the present invention.

Referring to FIG. 7, in another embodiment of the needle device 10 according to the present invention, the nozzle 30 consists of a base member 31, such as a cylindrical member, having a base longitudinal axis 735 axially disposed through the center of the base member 31, a proximal end 733 and a distal end face 731; and an auxiliary cylindrical member 32, having an auxiliary longitudinal axis 736 axially disposed through the center of the auxiliary member 32, a proximal end 734 and a distal end face 732. The diameter of the base cylindrical member 31 is in the range from about 0.050 inches to 0.275 inches, preferably from about 0.100 inches to 0.120 inches. The diameter of the auxiliary cylindrical member 32 in the range from about 0.050 inches to 0.090 inches, preferably from about 0.060 inches to 0.080 inches. The auxiliary cylindrical member 32 extends axially from the distal end face 731 of the base cylindrical member 31. The length of the auxiliary cylindrical member 32 is in the range from about 0 inches to 0.100 inches, preferably from about 0.125 inches to 0.500 inches. In one embodiment of the nozzle 30, the center auxiliary axis 736 is substantially parallel to and offset from the central base axis 735.

Referring still to FIG. 7, in a particular embodiment, the distal end face 731 of the base cylindrical member 31 is substantially perpendicular to the central base axis 735. The distal end face 732 of the auxiliary cylindrical member 32 is positioned at an angle β between 0° and 90° clockwise from the auxiliary axis 736, preferably between 15° and 30°, thereby forming a tissue piercing point 310 at the distal end 316 of the nozzle 30.

The tissue piercing point 310 is adapted to penetrate body tissues, including skin, rectus, bladder wall and bladder neck. In one embodiment of the invention, the tissue piercing point 310 is reinforced to improve, for example, edge holding, durability and strength of the tissue piercing point 310.

With continued reference to FIG. 7, the first lumen 320 and the second lumen 330 are disposed axially in the nozzle 30. The first lumen 320 extends from the proximal end 733 of the base cylindrical member 31 to the distal end face 732 of the auxiliary cylindrical member 32. The second lumen 330 extends from the proximal end 733 of the base cylindrical member 31 to the distal end face 731 of the base cylindrical member 31. In a particular embodiment, the first lumen 320 and the second lumen 330 are substantially parallel to the central base axis 735 and to the auxiliary axis 736 of the nozzle 30. As described above in the embodiment of the needle device depicted in FIG. 1 and FIG. 3, the lumen 320 of the nozzle 30 illustrated in FIG. 7 is in fluid communication with the reservoir 60 through the supply tube 40 and the connector 54 in the handle 50. In another embodiment, the lumen 320 of the nozzle 30 illustrated in FIG. 7 is in fluid communication with the syringe 80 shown in FIG. 2 and described in the corresponding text, through a connecting tube 810, axially disposed in the port 75, and the connector 54.

Figure 8:
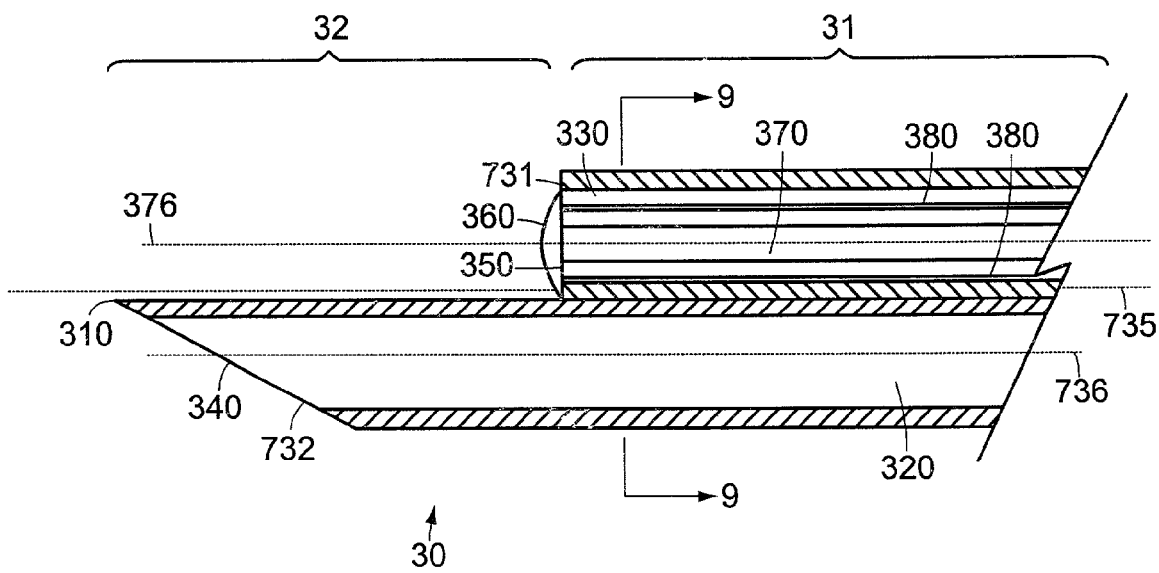
FIG. 8 illustrates an enlarged longitudinal cross-sectional view of the distal end of the nozzle according to the embodiment of the present invention shown in FIG. 7

Referring now to FIGS. 7 and 8, in this embodiment of the invention, the first lumen 320 has a first opening 340 in the distal end face 732 of the auxiliary cylindrical member 32 proximal and adjacent to the tissue piercing point 310. The second lumen 330 has a second opening 350 at the distal end face 731 of the base cylindrical member 31 and adjacent to the proximal end 734 of the auxiliary cylindrical member 32. In one embodiment of the invention, the second opening 350 is substantially perpendicular to the central base axis 735 of the base cylindrical member 31 of the nozzle 30.

As described above in the embodiment of the needle device depicted in FIGS. 3 and 4, the plurality of illumination-transmitting rods 380 and the image transmitting fiber-optic bundle 370, having an axis 376 axially disposed through the center thereof, are disposed within the second lumen 330. In a particular embodiment illustrated in FIGS. 7 and 8, the tissue piercing point 310 lies in the cross-sectional plane of the nozzle 30, defined by the central base axis 735 of the base cylindrical member 31 and the auxiliary axis 736 of the auxiliary member 32, and is positioned in that plane between the auxiliary axis 736 and the axis 376.

Referring to FIG. 8, the lens system 360 is joined to the distal end face 731 of the base cylindrical member 31 at the second opening 350. As described above, the lens system 360 includes, for example, a wide-angle plano-convex lens made from any suitable material, such as glass.

Figure 9:
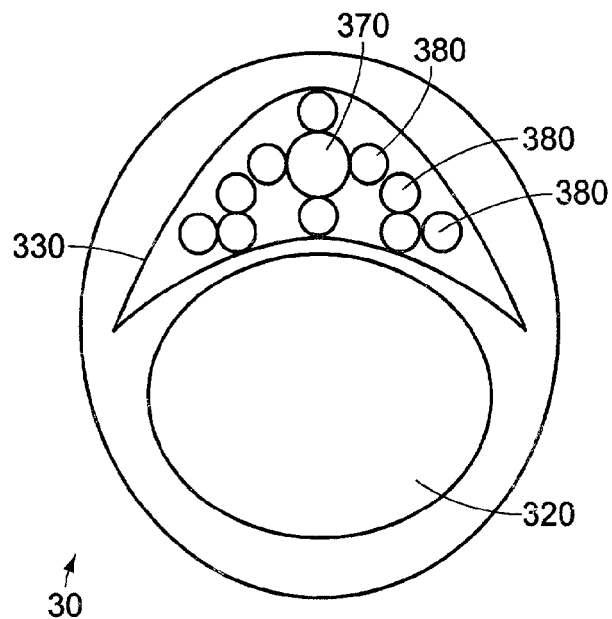
FIG. 9 illustrates a cross-sectional view along the line 9-9 of FIG. 8 according to another embodiment of the invention.

Referring to FIG. 9, the image transmitting bundle 370 of fiber-optic fibers and a plurality of illumination transmitting fiber-optic fibers 380 are disposed within the second lumen 330. As described above with regard to the embodiment illustrated in FIGS. 3-5, the image transmitting fiber-optic bundle 370 and illumination transmitting fiber-optic fibers 380 are connected to the light source 57 and the ocular system 59 shown in FIG. 1, respectively, to enable visualization of the tissue piercing point 310 through the ocular system 59.

Figure 10A:
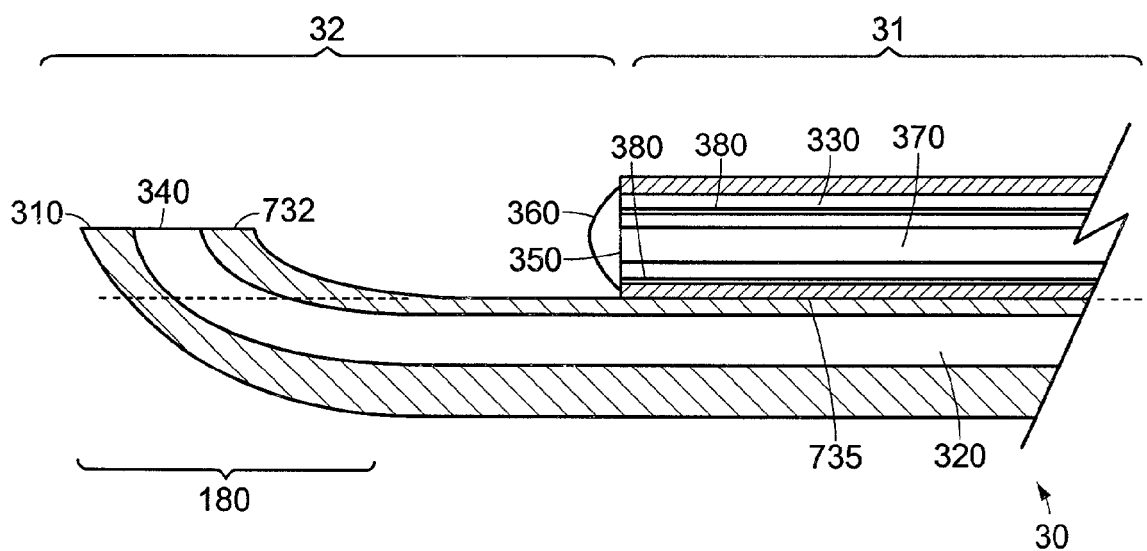
FIG. 10A illustrates an enlarged longitudinal cross-sectional view of the distal end of the nozzle according to yet another embodiment of the present invention.

Referring to FIG. 10a, in yet another embodiment of the nozzle 30 according to the invention, a distal end portion 180 of the auxiliary cylindrical member 32 forms a curve with the convex surface of the curve disposed on the side of the auxiliary cylindrical member 32 furthest from the central base axis 735. The distal end face 732 of the auxiliary cylindrical member 32 and the first opening 340 are substantially parallel to the center base axis 735 of the nozzle 30. The tissue piercing point 310 is located at the distal end of the distal end face 732 of the auxiliary cylindrical member 32. In the embodiment illustrated in FIG. 10a, the second opening 350 is substantially perpendicular to the center base axis 735 of the base cylindrical member 31 of the nozzle 30 and substantially perpendicular to the first opening 340.

Figure 10B:
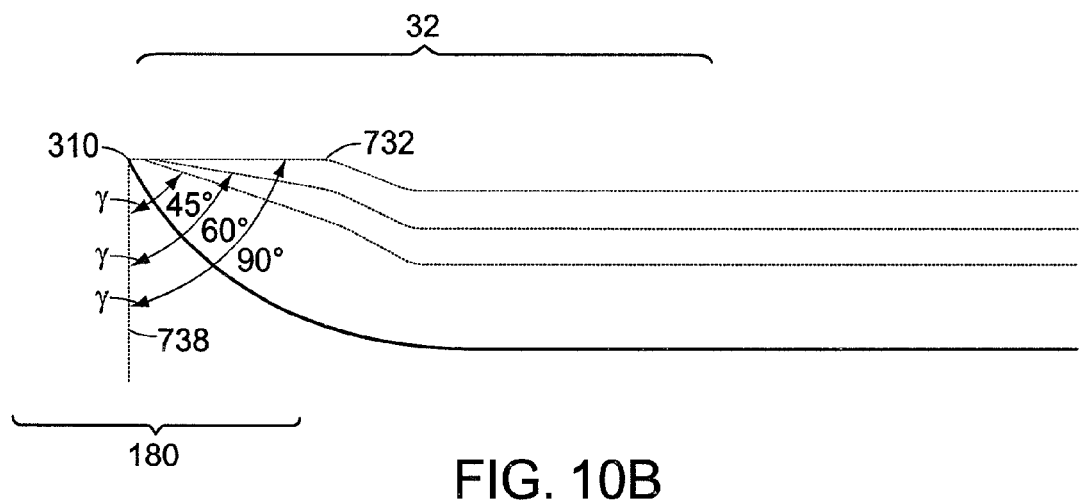
FIG. 10B illustrates an enlarged longitudinal cross-sectional view of the distal end of the nozzle according to still another embodiment of the present invention.

As illustrated in FIG. 10B, in another embodiment of the invention, the distal end face 732 may be positioned at an angle γ to a perpendicular 738 from the center base axis 735 drawn from the tissue piercing point 310 between 0° and 90°. In one embodiment, the angle γ equals 90°. In another embodiment, the equals 60°. In yet another embodiment, the angle γ equals 45°.

Figure 11:
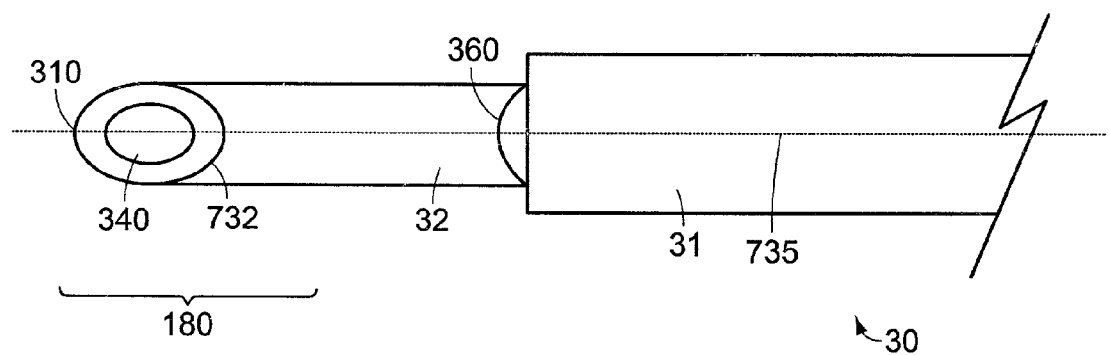
FIG. 11 illustrates a top view of the distal end of the nozzle according to the embodiments of the present invention shown in FIGS. 10A and 10B.

Referring to FIG. 11, in the embodiments of the nozzle 30 described above and illustrated in FIGS. 10a and 10b, the position of the lens 360 relative to the tissue piercing point 310 and the first opening 340 permits an operator to observe both the tissue piercing point 310 as it advances in the patient's body, and the first opening 340.

The needle device 10 of the present invention can be useful in a variety of medical procedures. For example, staghorn calculi trapped in the renal pelvis of a patient may become infected and may reform if all remnants of the stone are not removed during surgery. It is desirable to flush the renal pelvis to remove all of the stone fragments.

Figure 12A:
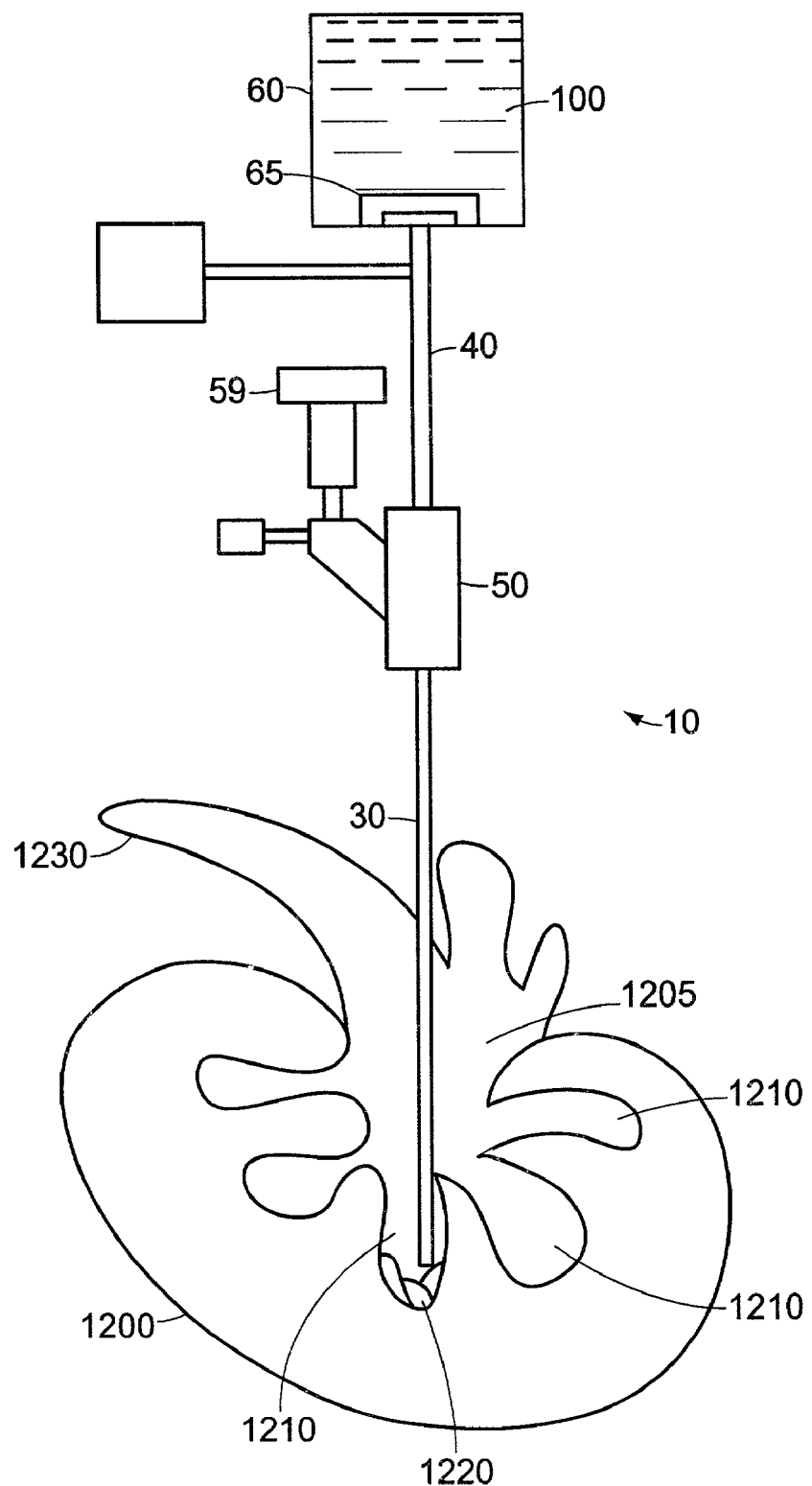
FIG. 12A illustrates positioning of the nozzle in a method for removing calculi from a kidney using the needle device of the present invention.

Referring now to FIG. 12A, in another aspect the invention includes a method for removing material from the body, for example, for removing calculi 1220 from a kidney 1200. In one embodiment of the invention, the method includes the steps of providing the needle device 10 described above with the nozzle 30 dimensioned to fit within a renal calyx 1210. The nozzle 30 of the needle device 10 is inserted by an operator through a flank incision into the abdomen, and then into the renal pelvis 1205 of the kidney 1200 of a patient. The distal end of the nozzle 30 is visualized through the ocular system 59. After the needle device 10 is inserted into the renal pelvis 1205, the operator visualizes the renal calyx 1210 and advances the distal end 316 of the nozzle 30 in close proximity to the calculi 1220 in the renal calyx 1210. The operator activates the pressurizer 65, which transports fluid 100 from reservoir 60 under pressure through the supply tube 40 and the lumen 320, and directs the pressurized fluid 100 through the first opening 340 onto the calculi 1220. The calculi 1220 are flushed from the renal calyx 1210 into the renal pelvis 1205 where the calculi 1220 are aspirated or pass freely from the kidney 1200 to the urethra 1230, and out of the patient's body.

In another embodiment, the needle device 10 can be used to treat intrinsic sphincter deficiency ("ISD"), which is a medical condition that is characterized by stress incontinence and has been associated with a weak urethral sphincter that is unable at rest to adequately close the urethra. Treatment of this condition typically entails injection of a bulking material, such as, for example, collagen, silicone particles, ceramic balls, or fluoropolymer particles, for example, polytetrafluoroethylene particles sold under the trademark TEFLON® by E.I. du Pont de Nemours and Company of Wilmington, Del., to obstruct the lumen of the urethra to prevent urine outflow.

Figure 12B:
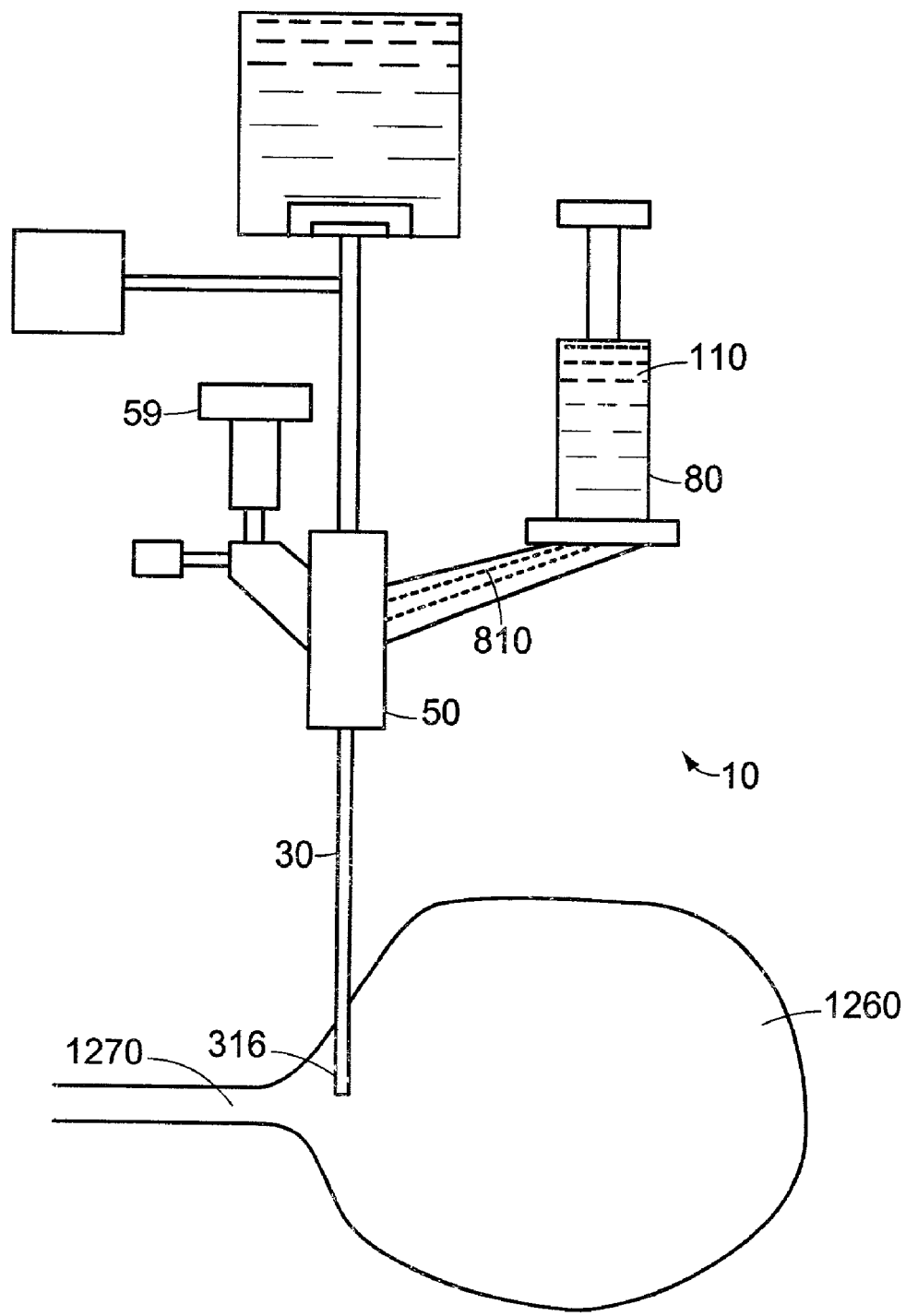
FIG. 12B illustrates positioning of the nozzle in a method for injecting bulking material using the needle device of the present invention

Referring to FIG. 12B, the method for injecting a bulking material 110 includes providing a needle device 10 having a syringe 80 containing the bulking material 110. The operator inserts the tissue piercing point 310 of the nozzle 30 using handle 50 through a flank incision into the abdomen of a patient, and then into the bladder 1260, while visualizing the distal end 316 of the nozzle 30 through the ocular system 59. After the needle device 10 is inserted into the bladder 1260, the operator locates the bladder neck 1270 visually and inserts the tissue piercing point 310 at the distal end 316 of the nozzle 30 through the wall of the bladder neck 1270 until the tissue piercing point 310 is in the submucosal tissues as determined visually via optical system 59. The operator activates the syringe 80 containing bulking material 110, and injects bulking material 110 from the barrel of the syringe 80 through the connecting tube 810, into the lumen 320 of the nozzle 30, and through the first opening 340 near the tissue piercing point 310 into the submucosal tissues of the urethra, the bladder neck, and/or into peri-urethral tissues proximal to the urethra. Bulking material 110 is injected into the tissue until the operator determines visually that the urethral sphincter muscle is coapted and able to maintain sufficient resting closing pressure to prevent urine from involuntarily leaking from the distal urethral orifice of the patient.

It can be appreciated that this method of the invention is not limited to the embodiments described above and shown in FIGS. 12A-12B. The method according to the invention can also be applied to other internal surfaces in the body to flush, irrigate, cut, or debride tissue, such as diverticular or fistular tissue, or to inject fluids into tissues in the patient's body.

Figure 13:
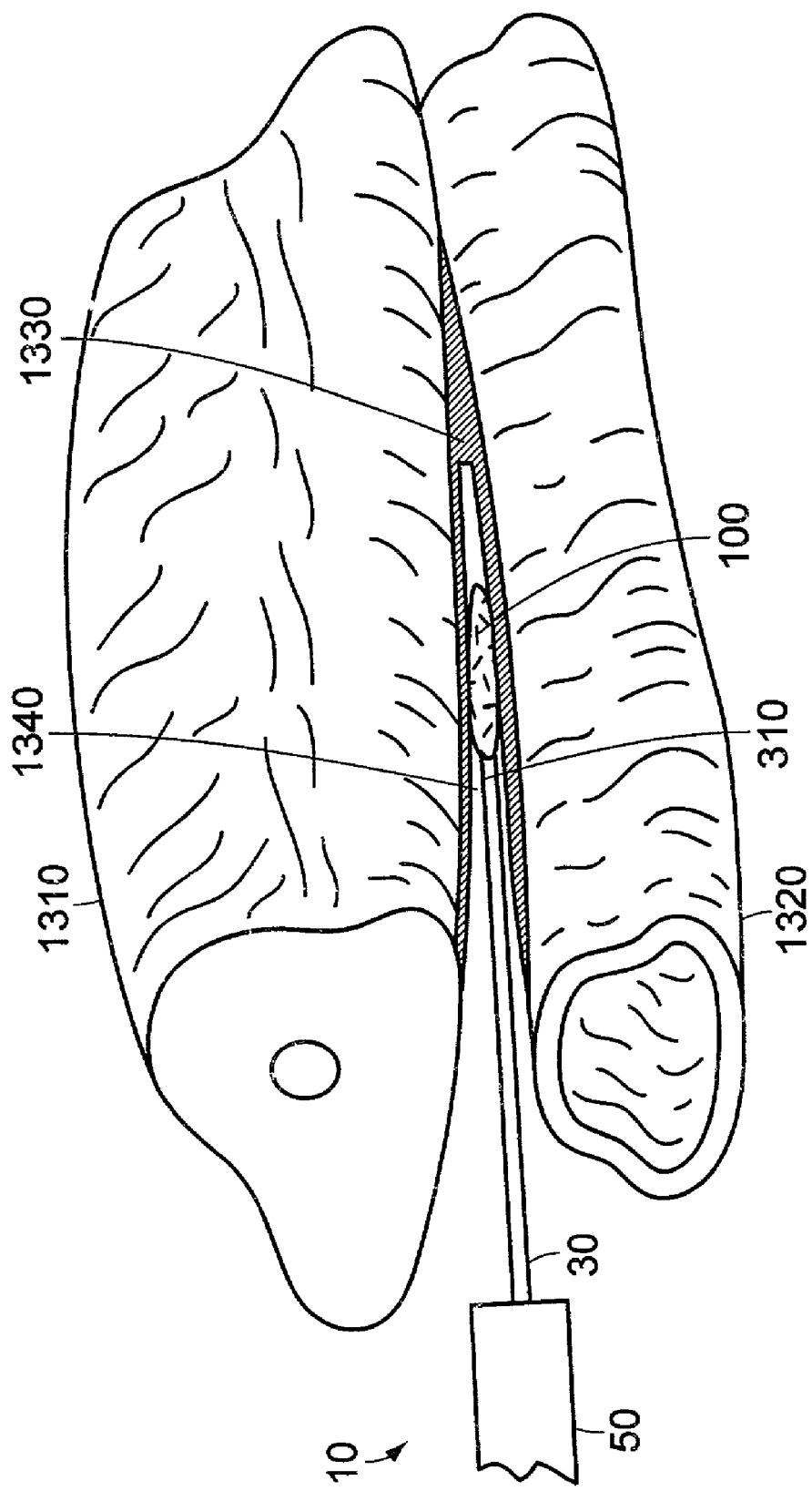
FIG. 13 illustrates positioning of the nozzle in a method for separating tissue planes using the needle device of the present invention.

The needle device of the present invention can also be used in the course of retropubic radical laparoscopic prostatectomy, a standard surgical procedure for patients with organ confined prostate cancer. During this procedure, it is highly desirable to maintain the neuro-vascular bundle of the prostate intact to preserve sexual function. The nerve sparing technique is difficult because this bundle is located under the prostate and out of the field of vision of the laparoscope. Referring to FIG. 13, in one embodiment of the invention, the method for hydrodissecting tissue planes, more particularly, for example, for separating the prostate 1310 from the ventral surface of the rectum 1320, includes the steps of providing the needle device 10 described herein, inserting the nozzle 30 using the handle 50 until the tissue piercing point 310 is in the biplane fascial layer 1330, known as Denonvillers fascia and located between the dorsal surface of the prostate 1310 and the ventral surface of the rectum 1320, and, as described above, injecting a fluid or a gas at a sufficient force into Denonvillers fascia to generate a fluid-filled or gas-filled space 1340 to physically separate the prostate 1310 and the rectum 1320. This method can be practiced by a variety of surgical approaches, such as, for example, transperineally, transrectally, or suprapubically, and avoids substantially traumatizing the prostate neurovascular bundle It can be appreciated that the method of hydrodissecting is not limited to separating the prostate from the rectum, and may also be used separate muscle planes or to hydrodissect other tissue planes in the body, such as strictures or adhesions.

It will be apparent to those skilled in the art of medical devices that various modifications and variations can be made to the above-described structure and methodology without departing from the scope or spirit of the invention.

The invention claimed is:

1. A needle device, comprising:
   a supply tube having a proximal end and a distal end;
   a nozzle, comprising:
   a longitudinal axis, a proximal end,
   a distal end,
   a bevel at said distal end comprising a tissue piercing point,
   a first lumen axially disposed in said nozzle from said proximal end to said distal end, said first lumen at said proximal end of said nozzle in fluid communication with said distal end of said supply tube, said nozzle comprising a first opening at said distal end of said nozzle in fluid communication with said first lumen,
   a second lumen axially disposed in said nozzle from said proximal end to said distal end, said nozzle further comprising a second opening at said distal end of said nozzle in optical communication with said second lumen, wherein the first opening is distal to the second opening between the second opening and the tissue piercing point, and
   at least one optical element axially positioned in said second lumen for transmitting and receiving optical radiation through said second opening in said nozzle.

2. The device of claim 1 further comprising a pressurizer.

3. The device of claim 2 wherein said pressurizer intermittently pressurizes a fluid delivered through said first opening.

4. The device of claim 3 wherein said pressurizer further comprises a pulsatile flow generator; said pulsatile flow generator is selected from a group consisting of ultrasonic vibrator, valving system, gas-assist system, and piezoelectric actuator.

5. The device of claim 2 wherein said pressurizer is selected from a group consisting of a pneumatic pressurizer and a hydraulic pressurizer.

6. The device of claim 5 wherein said hydraulic pressurizer is selected from a group consisting of a bladder pump, a piston pump, and an impeller pump.

7. The device of claim 2 further comprising a pressurized gas.

8. The device of claim 1 wherein said nozzle is rigid.

9. The device of claim 1 further comprising a suction apparatus.

10. The device of claim 1 wherein said nozzle is detachable from said supply tube.

11. The device of claim 1 wherein said second opening is positioned proximal to said tissue piercing point and is substantially perpendicular to said longitudinal axis.

12. The device of claim 11 wherein said first opening is substantially parallel to said longitudinal axis.

13. The device of claim 12 wherein said first opening is substantially adjacent to said tissue piercing point.

14. The device of claim 1 wherein said optical element comprises a bundle of fiber-optic rods.

15. The device of claim 14 wherein said optical element further comprises a fish-eye lens.

16. The device of claim 1 further comprising a plurality of fiber-optics rods.

17. The device of claim 1 further comprising a handle at the proximal end of said nozzle.

18. The device of claim 17 wherein said handle at the proximal end of said nozzle further comprises a port for affixing said optical element to said nozzle.

19. The device of claim 17 further comprising a reservoir for holding bulking implant.

20. The device of claim 19 wherein said bulking implant is selected from a group consisting of collagen, silicone particles, ceramic balls, and fluoropolymer particles.

21. The device of claim 20 wherein said handle comprises a port for affixing said reservoir to said nozzle.

22. The device of claim 1 wherein said tissue piercing point of said nozzle is adapted to penetrate skin, rectus, bladder wall and bladder neck of a patient.

23. The device of claim 1 wherein said tissue piercing point is reinforced.

* * * * *